United States Patent
Rao et al.

(10) Patent No.: US 6,197,532 B1
(45) Date of Patent: Mar. 6, 2001

(54) DIAGNOSIS AND DETECTION OF BREAST CANCER AND OTHER CANCERS

(75) Inventors: Prakash N. Rao, Kenner; Madhwa H. G. Raj, New Orleans, both of LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/234,434

(22) Filed: Jan. 20, 1999

Related U.S. Application Data

(60) Provisional application No. 60/122,048, filed on Jan. 22, 1998.

(51) Int. Cl.[7] .................................................. G01N 33/535
(52) U.S. Cl. .................... 435/7.92; 435/7.1; 435/7.23; 435/7.9; 435/7.94; 435/188; 530/350; 530/388.25; 530/388.85; 530/391.3
(58) Field of Search ................................. 435/7.23, 7.92, 435/7.1, 188, 7.9, 7.94; 530/387.1, 350, 388.25, 388.85, 391.3

(56) References Cited

U.S. PATENT DOCUMENTS

| | | |
|---|---|---|
| 4,444,744 | 4/1984 | Goldenberg . |
| 4,851,510 | 7/1989 | Khan . |
| 5,001,225 | 3/1991 | Taylor . |
| 5,798,257 | 8/1998 | Zain et al. . |

OTHER PUBLICATIONS

Adiga, P. et al., "Biochemical and immunological aspects of riboflavin carrier protein," *J. Biosci.*, vol. 13, pp. 87–104 (1988).

Adiga, R. et al., "Carrier protein mediated transplacental riboflavin transport in the primate," pp. 129–140 in N. Moudgal et al. (eds.), *Perspectives in Primate Reproductive Biology* (1991).

Natraj, U. et al., "Isolation and partial characterisation of human riboflavin carrier protein and the estimation of its levels during human pregnancy," *J. Reprod. Immunol.*, vol. 13, pp. 1–16 (1988).

Ramesh Babu, P. et al., "Evidence for estrogen–induced riboflavin carrier protein in sera of human breast cancer: its correlation with estrogen receptor status," *Med. Sci. Res.*, vol. 24, pp. 37–39 (1996).

*Primary Examiner*—Sheela Huff
*Assistant Examiner*—Larry R. Helms
(74) *Attorney, Agent, or Firm*—John H. Runnels

(57) ABSTRACT

Measurements of elevated levels of riboflavin carrier protein (RCP) can be used to detect breast, liver, ovarian, and endometrial cancers. Stains for riboflavin carrier protein can be used to visualize malignancies in tissue specimens. The new technique is particularly well-suited for the early detection of breast cancer. With a radioimmunoassay for RCP, we have observed that serum RCP levels were significantly elevated in women with breast cancer as compared to control subjects. A serum RCP level $\geq 1.0$ ng/ml was highly predictive of the presence of breast cancer (other than in pregnant females).

15 Claims, No Drawings

SEQUENCE LISTING

```
<160> NUMBER OF SEQ ID NOS:  2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  PCR primer

<400> SEQUENCE: 1
cccagaagga cagcaaaaga                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  PCT primer

<400> SEQUENCE: 2
caagcagagg caggaggatt                                                  20
```

DIAGNOSIS AND DETECTION OF BREAST CANCER AND OTHER CANCERS

The benefit of the Jan. 2, 1998 filing date of provisional application 60/122,048 is claimed under 35 U.S.C. §119(e).

This development of this invention was partially supported by the Government under grant number 1RO3CA71743-01 awarded by the National Cancer Institute. The Government has certain rights in this invention.

This invention pertains to the diagnosis and detection of breast cancer and other cancers.

Breast cancer is the second most common cause of cancer-related death after lung cancer, and remains the leading cause of cancer-related death in women between the ages of 40 and 55. Early detection and diagnosis is associated with significantly improved long-term survival. It is therefore of critical importance to identify screening markers that can accurately and reliably detect breast cancer.

Riboflavin, one of the B vitamins, is essential for cell growth and development. The transport and subsequent deposition of riboflavin in developing cells is facilitated by an estrogen-induced phosphoglycoprotein called riboflavin carrier protein (RCP). RCP binds riboflavin in a 1:1 molar ratio.

In pregnancy studies in rodents and primates, immunological interference with RCP to inhibit riboflavin transport to the developing embryo has been reported to cause acute fetal wastage and miscarriage. See R. Adiga et al., "Carrier protein mediated transplacental riboflavin transport in the primate," pp. 129–140 in N. Moudgal et al. (eds.), *Perspectives in Primate Reproductive Biology* (1991).

P. Ramesh Babu et al., "Evidence for estrogen-induced riboflavin carrier protein in sera of human breast cancer: its correlation with estrogen receptor status," *Med. Sci. Res.*, vol. 24, pp. 37–39 (1996) studied the presence of riboflavin carrier protein in human breast cancer patients and stated, "In conclusion, our studies show that despite the correlation of circulatory RCP with the ER [estrogen receptor] status of breast cancer patients, its presence in low quantities in the circulation of the majority of patients failed to confirm its value as a potential marker in the management of human breast cancer."

Surprisingly, we have discovered a reliable, sensitive, and specific method to detect breast cancer and other cancers in humans and other mammals by specific measurements of elevated levels of riboflavin carrier protein in serum or other biological fluids. We have also prepared stains specific for riboflavin carrier protein that have been used to visualize malignancies in tissue specimens. The new technique is particularly well-suited for the early detection of breast cancer.

Using a highly sensitive radioimmunoassay, we have observed that serum RCP levels were significantly elevated in women with breast cancer (n=46) as compared to control subjects (n=19) (6.20±7.8 ng/ml versus 0.76±0.27 ng/ml, $p<0.05$). A serum RCP level ≧1.0 ng/ml was highly predictive of the presence of breast cancer, accurately detecting 89.2% of tumors in stages I and II and 100% of tumors in stages III and IV. Overall this RCP-based test had a sensitivity of 91%, a specificity of 74%, and a positive predictive value of 89%.

Materials and Methods

Assurances. The protocol and patient consent forms were reviewed and approved by the Institutional Review Board of the Louisiana State University Medical Center, New Orleans, La.

Patient Selection. A total of 65 women were studied, including 46 with intact breast tumors and 19 controls. The breast cancer patients were consecutively recruited from the surgical oncology clinic at the Louisiana State University Medical Center in New Orleans (i.e., recruited consecutively as they were seen in the clinic, without any pre-selection). Control subjects were selected from the staff of the Louisiana State University Medical Center, and each was confirmed to be cancer-free. Blood samples were drawn in a serum separator tube (Becton Dickinson #6150, vacutainer system, Rutherford N.J.), assigned a code number, and transported to the laboratory. The study was carried out in a double-blind fashion, with the laboratory personnel unaware of a patient's clinical history, and the clinicians unaware of measured serum RCP levels.

Serum RCP Levels. Serum RCP levels were measured by a highly sensitive radioimmunoassay developed in our laboratory. The sensitivity of the assay is approximately 250 pg. The assay is specific for RCP. Other immunological detection methods known in the art could be used in lieu of the radioimmunoassay, such as ELISA, a competitive binding assay, binding to monoclonal antibodies to epitopes of RCP, binding to antibodies raised against natural or synthetic peptide analogs of regions of RCP, and binding to a mimetic of any of the above antibodies.

A sensitive and specific radioimmunoassay (RIA) has been developed using antiserum to chicken RCP and highly purified human RCP as standards. Briefly, highly purified RCP was radio-iodinated using Chloramine-T as the oxidizing agent. Twenty-five $\mu$l of Chloramine-T in 25 $\mu$l of phosphate buffer, pH 7.2 was added to a mixture of 1 mCi $Na^{125}I$ in 5 $\mu$l of buffer, 20 $\mu$l 0.1 M phosphate buffer pH 7.2, and 2.5 $\mu$g RCP, on an ice bath. After 60 seconds, the reaction was terminated by adding 100 $\mu$g sodium metabisulphite in 25 $\mu$l of phosphate buffer. The mixture was separated on a 10 ml Sephadex G-50 column with 0.1% gelatin in PBS. One milliliter fractions were collected and counted using a gamma spectrometer. The iodinated protein was seen to elute in fractions 3–6, followed by the free iodine fraction in tubes 8–11.

A competitive radioimmunoassay was performed by incubating 40 to 50,000 cpm of the labelled RCP with increasing amounts of unlabeled RCP (100 pg to 50 ng) and specific rabbit anti-RCP at 1:16,000 final dilution, in a total volume of 0.4 ml. Bound RCP was separated from free RCP using affinity purified goat anti-rabbit gamma globulin as the precipitating antibody (Antibodies, Inc., Cat. #48-156-3U, Davis, Calif.). This anti-rabbit IgG was affinity purified to be free of cross-reactivity with human, bovine, and mouse IgG. A standard curve was fitted using an on-line weighted log-logit analysis. The curve had a sensitivity of 250 pg, with a correlation coefficient of 0.994 and a slope of −1.044.

The RIA was highly specific for RCP, and did not react with other vitamin-binding proteins such as folate binding protein (FBP) or retinol binding protein (RBP). It is believed that the use of the affinity purified anti-rabbit IgG, free of cross-reactivity with human, bovine, and mouse IgG, was an important factor in the success of this technique. Without the affinity purification, cross-reactivity with other antigens compromise the results. Prior to our adoption of this purification step, our results had not been reproducible. Other highly specific immunological assays should also be successful, so long as care is taken to minimize cross-reactivities.

Other detectable labels that may be used are labels such as those known in the art, including a radioactive material, a fluorophore, a dye, an electron-dense compound, or an enzyme.

Statistical Analysis. Statistical analyses of data were performed by analysis of variance (ANOVA) using Bonferroni's post hoc test after a logarithmic normalization of the data, following the statistical procedures of B. Rosner, *Fundamentals of Biostatistics* (1986).

Immunohistochemical localization of RCP in breast cancer tissue. Breast tissue samples obtained during surgery from tumors that varied between Stages II–IV were fixed in 5% paraformaldehyde, and blocked in paraffin. Five-micron sections were examined for RCP using otherwise standard immunohistochemical techniques. Briefly, paraffin was removed from tissue sections, the tissue sections were hydrated, and the tissue sections were reacted with primary rabbit anti-RCP antibody. The primary antibody was followed by reactions with biotinylated goat anti-rabbit gamma globulin, avidin-peroxidase conjugate, and chromogen-substrate (amino ethyl carbazole-AEC) to develop a bright red color (Zymed Co., Lexington, Ky.). Non-specific controls included a slide omitting the primary antibody, and a slide with pre-immune rabbit serum substituted for the primary antibody. Another slide was used to demonstrate the disappearance of specific localization upon absorption of the primary antibody by excess antigen. The sections were counter-stained with hematoxylin, mounted and photographed.

Results

Data are expressed as mean±standard deviation. In women with intact tumors, mean serum RCP levels were 6.20±7.8 ng/ml, significantly higher than the concentrations for control subjects, 0.76±0.27 ng/ml. See Table 1.

TABLE 1

Serum RCP Levels in Breast Cancer Patients and in Controls

| Group | n | Mean RCP Level (ng/ml) | Standard Deviation | 95% confidence interval for the mean | Total Range of Serum RCP Levels, all patients |
|---|---|---|---|---|---|
| Control | 19 | 0.76 | 0.27 | 0.63–0.89* | 0.5–1.3 |
| Breast Cancer Patients | 46 | 6.20 | 7.80 | 3.87–8.50* | 1.0–37.0 |

*$p < 0.05$ per Bonferronis post hoc test

Based on the range of RCP levels in the controls, 0.63–0.89 ng/ml, a "cutoff" serum RCP level of $\geq 1.0$ ng/mnl was selected as a predictor of the presence of tumors. Table 2 gives the specificity, sensitivity, and positive and negative predictive values using this of 1.0 ng/ml cutoff value.

TABLE 2

Predictive Value of RCP Test Using a 1.0 ng/ml Cutoff (n = 65)

| | % with intact tumor | Sensitivity (%) | Specificity (%) | Positive Predictive Value (%) | Negative Predictive Value (%) |
|---|---|---|---|---|---|
| Total | 70.8 (46/65) | 91.3 | 73.7 | 89.4 | 77.8 |
| Age | | | | | |
| <45 | 33.8 (22/65) | 92.3 | 66.7 | 80.0 | 85.7 |
| $\geq$45 | 66.2 (43/65) | 90.6 | 80.0 | 95.5 | 72.7 |
| Race | | | | | |
| White | 55.4 (36/65) | 95.5 | 100.0 | 100.0 | 83.3 |
| Non-White | 44.6 (29/65) | 87.5 | 64.3 | 80.8 | 75.0 |

Immunohistochemical examination vividly revealed increased RCP expression in the cytoplasm of the epithelial cells of the adenocarcinoma. By contrast, RCP expression in non-malignant tissue was confined to the ductular epithelium. A non-specific control in which non-immune serum was substituted for the RCP antiserum showed no localized staining.

Discussion

These results demonstrated increased expression of RCP in breast cancer tissue, and elevated serum levels of RCP in women with breast cancer. Mean serum levels of RCP were substantially and significantly higher than the levels that have previously been observed during the normal menstrual cycle or during normal pregnancy. See R. Adiga et al., "Carrier protein mediated transplacental riboflavin transport in the primate," pp. 129–140 in N. Moudgal et al. (eds.), *Perspectives in Primate Reproductive Biology* (1991); P. Adiga et al., "Biochemical and immunological aspects of riboflavin carrier protein," *J. Biosci.*, vol. 13, pp.87–104 (1988); and U. Natraj et al., "Isolation and partial characterisation of human riboflavin carrier protein and the estimation of its levels during human pregnancy," *J. Reprod. Immunol.*, vol. 13, pp. 1–16 (1988). Without wishing to be bound by this theory, we hypothesize that increased RCP serum levels in breast cancer patients reflect either increased hepatic production of RCP, or increased synthesis of RCP by the breast cancer cells.

In our study a cutoff RCP serum level of $\geq 1.0$ ng/ml predicted the presence of tumors of the breast with great accuracy, correctly predicting 89.2% (33/37) tumors in stages I and II, and 100% (9/9) of those in stages III and IV. Overall the RCP test demonstrated a sensitivity of 91%, a specificity of 74% and a positive predictive value of 89%. For comparison, recent studies have reported that a combination of physical examination and mammography has a sensitivity of 95%, a specificity of 51%, and an overall predictive value of 77%; and that needle localized breast biopsies have an accuracy rate of 20–40%. Further advantages of the RCP test are that it is non-invasive, does not require sophisticated instrumentation, and is less subject to errors of interpretation. Note that pregnant females have elevated RCP levels, meaning either that the "cutoff" level would have to be revised appropriately for pregnant females, or that the assay is not appropriate for use in pregnant females.

These properties of the RCP test also allow it to be used to assess the effectiveness of breast cancer therapy, and as an indicator of recurrent disease.

Other Estrogen Dependent Cancers

Preliminary data suggest that increased levels of riboflavin carrier protein are also associated with liver cancer and endometrial cancer. Other estrogen-sensitive cancers such as ovarian cancers should also show increased levels of riboflavin carrier protein. Thus these cancers may also be diagnosed by assays for RCP. A double-blind evaluation was made of RCP levels in serum from 33 subjects. Ten of these subjects had primary hepatocellular carcinomas, and twenty-three were controls. RCP was measured by the same sensitive radioimmunoassay described above. Mean serum RCP levels were markedly elevated in all ten hepatocellular carcinoma cases (20.18±22.31 ng/ml), as compared to controls (0.75±0.26 ng/ml, $p<0.001$). The total range of serum RCP levels in all cancer patients was 1.65 to 40.0 ng/ml. Immunohistochemical analysis also revealed positive staining for RCP in tissue samples taken from hepatocellular carcinomas.

Because elevated RCP serum levels have been seen in both breast cancer patients and liver cancer patients, measurement of an elevated RCP level may require differentiation between these possibilities. Such differential diagnosis is aided by the fact that breast cancer is about 100 times more common in women than in men, while liver cancer is about 6 times more common in men than. in women. Thus an elevated RCP level in women is more likely to be associated with breast cancer, while an elevated RCP level in men is more likely to be associated with liver cancer.
Increased Transcription of RCP Gene Preliminary data suggest that increased transcription of the RCP gene is found in estrogen-dependent cancers, and it is expected that increased transcription of the RCP gene will be predictive of increased susceptibility to such cancers, even in patients currently displaying no symptoms of cancer.

We have observed increased transcription of the RCP gene in human breast cancer tissue samples by semi-quantitative reverse transcriptase-polymerase chain reaction (RT-PCR). Human breast cancer tissue and control breast tissue were sectioned and stored at −70° C. until used. Total RNA was extracted from the tissue by disrupting and homogenizing approximately 40 mg of tissue in liquid nitrogen, followed by extraction using the EZNA™ total RNA kit (Omega Biotek, New Orleans, La.) according to the manufacturer's protocol. Approximately 5 μg total RNA was then reverse transcribed in a 30 μl reaction containing 1 μM of random hexamers, 1 mM dNTPs, 5 mM $MgCl_2$, 10 mM DTT, 50 mM KCl, 10 mM tris buffer pH 8, and 10 units AMV reverse transcriptase (Promega Corp.) for 1 hour at 42° C. One tenth of this reaction mixture was then amplified by PCR using 20 pM each of two primers derived from the published sequence for the chicken RCP gene, D. Zheng et al., "Chicken Riboflavin Binding Protein cDNA Sequence and Homology with Milk Folate Binding Protein," *J. Biol. Chem.*, vol. 263, pp. 11126 et seq. (1988). The forward primer (bases 25–44) was 5'-cccagaaggacagcaaaaga-3' (SEQ ID NO. 1). The reverse primer (bases 624–605) was 5'-caagcagaggcaggaggatt-3' (SEQ ID NO. 2). PCR amplification for 35 cycles was carried out in a 100 μl reaction chamber under standard conditions. A 600 base pair product was visualized by electrophoresis in a 2% agarose/ethidium bromide gel. More amplification product was seen from the cancer tissue specimen than from the control specimen.

The complete disclosures of all references cited in this specification are hereby incorporated by reference. In the event of an otherwise irreconcilable conflict, however, the present specification shall control.

We claim:

1. A method for detecting in a mammal a cancer selected from the group consisting of breast cancer, liver cancer, ovarian cancer, and endometrial cancer; comprising measuring the concentration of riboflavin carrier protein in a specimen from the mammal by specific immunoassay; wherein an elevated concentration of riboflavin carrier protein indicates a likelihood that the mammal has cancer.

2. A method as recited in claim 1, wherein the specimen comprises serum.

3. A method as recited in claim 1, wherein said immunoassay comprises reacting both a fluid from the mammal and labelled riboflavin carrier protein with a specific anti-riboflavin carrier protein antibody; precipitating antibody-bound riboflavin carrier protein with a second antibody that specifically binds the anti-riboflavin carrier protein antibody but that does not bind components of the serum; and measuring the amount of label present in the resulting precipitate.

4. A method as recited in claim 1, wherein said immunoassay comprises a specific enzyme-linked immunosorbent assay.

5. A method as recited in claim 1, wherein said method is used to detect breast cancer.

6. A method as recited in claim 5, wherein the mammal is not a pregnant female, wherein the specimen comprises serum, and wherein a serum concentration of riboflavin carrier protein greater than 1.0 ng/ml is considered an elevated concentration of riboflavin carrier protein.

7. A method as recited in claim 1, wherein said method is used to detect liver cancer.

8. A method as recited in claim 7, wherein the mammal is not a pregnant female, wherein the specimen comprises serum, and wherein a serum concentration of riboflavin carrier protein greater than 1.0 ng/ml is considered an elevated concentration of riboflavin carrier protein.

9. A method as recited in claim 1, wherein said method is used to detect endometrial cancer.

10. A method as recited in claim 1, wherein said method is used to detect ovarian cancer.

11. A method for detecting tumorous portions of a mammalian breast, liver, ovarian, or endometrial tissue specimen, comprising reacting the specimen with an antibody specific for riboflavin carrier protein, and observing portions of the specimen to which the antibody preferentially binds.

12. A method as recited in claim 11, wherein the tissue specimen comprises breast tissue.

13. A method as recited in claim 11, wherein the tissue specimen comprises liver tissue.

14. A method as recited in claim 11, wherein the tissue specimen comprises ovarian tissue.

15. A method as recited in claim 11, wherein the tissue specimen comprises endometrial tissue.

* * * * *